(12) United States Patent
Santiago et al.

(10) Patent No.: US 11,851,647 B2
(45) Date of Patent: *Dec. 26, 2023

(54) CAPILLARY BARRIERS FOR STAGED LOADING OF MICROFLUIDIC DEVICES

(71) Applicant: The Board of Trustees of the Leland Stanford Junior University, Stanford, CA (US)

(72) Inventors: Juan G Santiago, Stanford, CA (US); Lewis A. Marshall, Pleasanton, CA (US); Anita Rogacs, Los Altos, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 243 days.

This patent is subject to a terminal disclaimer.

(21) Appl. No.: 16/998,839

(22) Filed: Aug. 20, 2020

(65) Prior Publication Data

US 2021/0062181 A1    Mar. 4, 2021

Related U.S. Application Data

(63) Continuation of application No. 16/192,034, filed on Nov. 15, 2018, now Pat. No. 10,787,660, which is a
(Continued)

(51) Int. Cl.
*C12N 15/10* (2006.01)
*B01L 3/00* (2006.01)
(Continued)

(52) U.S. Cl.
CPC .......... *C12N 15/101* (2013.01); *B01D 57/02* (2013.01); *B01L 3/502715* (2013.01);
(Continued)

(58) Field of Classification Search
None
See application file for complete search history.

(56) References Cited

U.S. PATENT DOCUMENTS

| 4,426,451 | A | 1/1984 | Columbus |
| 5,629,414 | A | 5/1997 | Boothroyd et al. |

(Continued)

FOREIGN PATENT DOCUMENTS

| CA | 2304641 C | 9/2003 |
| CN | 1326549 A | 12/2001 |

(Continued)

OTHER PUBLICATIONS

Garcia-Schwarz, G. et al. On-chip Isotachophoresis for Separation of Ions and Purification of Nucleic Acids, Journal of Visualized Experiments, 61, e3890, pp. 1-8 (Year: 2012).*
(Continued)

*Primary Examiner* — Xiaoyun R Xu
(74) *Attorney, Agent, or Firm* — Crawford Maunu PLLC (57) ABSTRACT

Various aspects of the present disclosure are directed toward methods and apparatuses for interacting a first liquid and a second liquid in one or more fluidic channels of a capillary structure. The methods and apparatuses can include providing at least one capillary barrier that positions a meniscus of the first liquid at a fluid-interface region using capillary forces within the capillary structure. Additionally, a path is provided along one of the channels for the second liquid to flow toward the fluid-interface region. Additionally, gas pressure is released, via a gas-outflow port, from the fluid-interface region while flow of the first liquid is arrested. Further, the first liquid and the second liquid contact in the fluid-interface region with the capillary barrier holding the first liquid at the fluid-interface region.

33 Claims, 10 Drawing Sheets

Related U.S. Application Data continuation of application No. 15/853,370, filed on Dec. 22, 2017, now Pat. No. 10,233,441, which is a continuation of application No. 14/213,832, filed on Mar. 14, 2014, now abandoned.

(60) Provisional application No. 61/785,255, filed on Mar. 14, 2013.

(51) Int. Cl.
*B01D 57/02* (2006.01)
*C12Q 1/6806* (2018.01)
*G01N 27/447* (2006.01)

(52) U.S. Cl.
CPC ... *B01L 3/502723* (2013.01); *B01L 3/502738* (2013.01); *C12Q 1/6806* (2013.01); *B01L 2200/027* (2013.01); *B01L 2200/0621* (2013.01); *B01L 2200/0631* (2013.01); *B01L 2200/0684* (2013.01); *B01L 2200/10* (2013.01); *B01L 2300/0838* (2013.01); *B01L 2300/0858* (2013.01); *B01L 2300/0867* (2013.01); *B01L 2300/12* (2013.01); *B01L 2300/165* (2013.01); *B01L 2400/0406* (2013.01); *B01L 2400/0421* (2013.01); *B01L 2400/0688* (2013.01); *B01L 2400/086* (2013.01); *B01L 2400/088* (2013.01); *G01N 27/44791* (2013.01)

(56) References Cited

U.S. PATENT DOCUMENTS

| | | |
|---|---|---|
| 5,631,128 A | 5/1997 | Kozal et al. |
| 5,650,268 A | 7/1997 | Kozal et al. |
| 5,827,415 A | 10/1998 | Gur et al. |
| 5,856,086 A | 1/1999 | Kozal et al. |
| 5,859,196 A | 1/1999 | Boothroyd et al. |
| 5,992,820 A | 11/1999 | Fare et al. |
| 6,130,098 A | 10/2000 | Handique et al. |
| 6,143,248 A | 11/2000 | Kellogg et al. |
| 6,296,020 B1 | 10/2001 | McNeely et al. |
| 6,561,224 B1 | 5/2003 | Cho |
| 6,626,417 B2 | 9/2003 | Winger et al. |
| RE38,352 E | 12/2003 | Kozal et al. |
| 7,364,916 B2 | 4/2008 | Sundberg et al. |
| 7,429,354 B2 | 9/2008 | Andersson et al. |
| 7,591,936 B2 | 9/2009 | Sarrut |
| 7,951,278 B2 | 5/2011 | Santiago et al. |
| 8,037,903 B2 | 10/2011 | Wang et al. |
| 8,394,251 B2 | 3/2013 | Santiago et al. |
| 8,414,754 B1 | 4/2013 | Santiago et al. |
| 8,524,061 B2 | 9/2013 | Utz et al. |
| 8,562,804 B2 | 10/2013 | Santiago et al. |
| 8,597,590 B2 | 12/2013 | Yue et al. |
| 8,721,858 B2 | 5/2014 | Chambers et al. |
| 8,821,704 B2 | 9/2014 | Santiago et al. |
| 8,846,314 B2 | 9/2014 | Chambers et al. |
| 8,986,529 B2 | 3/2015 | Santiago et al. |
| 8,999,129 B2 | 4/2015 | Jung et al. |
| 9,057,673 B2 | 6/2015 | Rogacs et al. |
| 9,144,799 B2 | 9/2015 | Rose et al. |
| 9,151,732 B2 | 10/2015 | Santiago et al. |
| 9,285,340 B2 | 3/2016 | Jung et al. |
| 9,297,039 B2 | 3/2016 | Santiago et al. |
| 9,753,007 B1 | 9/2017 | Chambers et al. |
| 10,233,441 B2 | 3/2019 | Santiago et al. |
| 2002/0036018 A1 | 3/2002 | McNeely et al. |
| 2004/0063217 A1 | 4/2004 | Webster et al. |
| 2006/0002817 A1 | 1/2006 | Bohm et al. |
| 2009/0282978 A1 | 11/2009 | Jensen et al. |
| 2011/0104816 A1 | 5/2011 | Pollack et al. |
| 2011/0290648 A1 | 12/2011 | Majlof et al. |
| 2012/0097272 A1 | 4/2012 | Vulto et al. |
| 2015/0037784 A1 | 2/2015 | Rogacs et al. |
| 2016/0153934 A1 | 6/2016 | Santiago et al. |
| 2016/0160208 A1 | 6/2016 | Santiago et al. |
| 2016/0209360 A1 | 7/2016 | Santiago et al. |

FOREIGN PATENT DOCUMENTS

| | | |
|---|---|---|
| CN | 1548957 A | 11/2004 |
| CN | 1715929 A | 1/2006 |
| CN | 102395421 A | 3/2012 |
| CN | 103402641 A | 11/2013 |
| EP | 1932593 A1 | 6/2008 |
| EP | 2213364 A1 | 8/2010 |
| JP | 2012516414 A | 7/2012 |
| WO | 2009137415 A2 | 11/2009 |
| WO | 2012120101 A1 | 9/2012 |
| WO | 2014153092 A1 | 9/2014 |
| WO | 2017132630 A1 | 8/2017 |

OTHER PUBLICATIONS

CIPO. Examination Report dated Apr. 9, 2021 for related counterpart Canadian Patent Application No. 2,906,730, (4 pages).
EPO. "Extended European Search Report," for related European Patent Application No. 14769958.1, dated Jan. 17, 2017 (3 sheets).
Friend, J. et al. Fabrication of microfluidic devices using polydimethylsiloxane, 2010, Biomicrofluidics, vol. 4, pp. 026502 (1-5).
Hosokawa et al.. "Power-free poly(dimethylsiloxane) microftuidic devices for gold nanoparticle-based DNA analysis", Lab Chip, vol. 4, pp. 181-185, May 12, 2004. http://pubs.rsc.org/en/Content/Articlelanding/2004/LC/b403930k#! divAbstract>.entire document.
USPTO. International Search Report dated Jul. 29, 2014 for related PCT Patent Application No. PCT/US2014/029017.
Lee, G-8, et al. Microfluidic Chips for DNA Amplification, Electrophoresis Separation and On-Line Optical Detection, 2003, IEEE pp. 423-426.
Marshall L. A. et al. "An Injection-Molded Device for Purification of Nucleic Acids From Whole Blood Using Isotachophoresis." 2013 Annual Meeting of the AES, 8 pgs. (Nov. 2013).
Marshall L.A. and Santiago, J. G. "A Novel Device for Highly-Efficient Extraction of Nucleic Acids from 100 Microliter Whole Blood Samples." 2012 Annual Meeting of the AES, 4 pgs. (Oct. 31, 2012).
Marshall, et al., An injection molded microchip for nucleic acid purification from 25 microliter samples using Isotachophoresis. Journal of Chromatography A, 1331 (2014) 139-142.
USPTO. Office Action dated Mar. 10, 2017 for related U.S. Appl. No. 14/213,832.
USPTO. Office Action dated Aug. 24, 2017 for related U.S. Appl. No. 14/213,832.
Rogacs, A. et al., "Purification of nucleic acids using isotachophoresis", Journal of Chromatography A, 2014, vol. 1335, pp. 105-120.
CIPO. Search Report for related Chinese Patent Application No. 201480021876.2 dated Jun. 2, 2017, 2 pages.
UKIPO. Examination Report under Section 18(3) for related counterpart United Kingdom Patent Application No. 1517364.4, dated Mar. 20, 2019 (3 sheets).
CIPO. Examination Report for related counterpart Canadian Patent Application No. 2,906,730, dated Jul. 15, 2020 (6 pages).
IP Australia. Examination Report for related counterpart Australian Patent Application No. 2018206716, dated Sep. 26, 2019 (3 sheets).
EPO. Examination Report under Article 94(3) for related counterpart European Patent Application No. 14769958.1, dated Jul. 22, 2019 (5 sheets).
Garcia-Schwarz, G., et al. On-chip Isotachophoresis for Separation of Ions and Purification of Nucleic Acids, Journal of Visualized Experiments, vol. 61, pp. 1-8 (2012).
EPO. European Office Action dated Jan. 25, 2022 for related counterpart European Patent Application No. 14769958.1 (4 sheets).

(56) References Cited

OTHER PUBLICATIONS

AU-IPO. Australian Office Action dated Dec. 10, 2021 for related counterpart Australian Divisional Patent Application No. 2020239798 (8 sheets).
CNIPA. Office Action Notice dated Jun. 3, 2021 for related counterpart Chinese Divisional Patent Application No. 201910521030.X, with English translation (8 sheets).

* cited by examiner

CAPILLARY BARRIERS FOR STAGED LOADING OF MICROFLUIDIC DEVICES

FEDERALLY-SPONSORED RESEARCH AND DEVELOPMENT

This invention was made with Government support under contract HR0011-12-C-0080 awarded by the Defense Advanced Research Projects Agency. The U.S. Government has certain rights in this invention.

OVERVIEW

Loading microfluidic chips with multiple liquids is challenging in many ways. For example, loading can be challenging due to limited access to a microfluidic chip based on few sample ports. Additionally, channel dimensions can be on the order of 100 For such implementations, surface forces can become important because aqueous liquids will not advance into hydrophobic channels unless driven by an external pressure, and bubbles can become trapped if channels are loaded from multiple directions. Certain applications of the microfluidic chips include creating a liquid-to-liquid interface between multiple liquids. In these instances, the liquids to be loaded may have limited availability, such as liquids involving a rare cell or scarce DNA or RNA samples. It is therefore desirable to minimize fluid loss when creating the liquid-to-liquid interface.

Isotachophoresis (ITP) for nucleic acid purification is a sample preparation technique with a growing portfolio of applications. ITP can be used to isolate DNA from human blood, serum, and plasma. ITP can also be used for RNA purification from bacteria in urine and blood, and purification of small RNA from total RNA in kidney cells. ITP purification can be a valuable alternative to conventional solid-phase extraction and liquid-liquid extraction techniques for nucleic acid purification as it can extract from low abundance samples and does not require centrifugation or toxic chemistries.

SUMMARY

Various aspects of the present disclosure are provided to allow liquid interfaces created in microfluidic channels without loss of sample liquid. In connection with these and other aspects, the present disclosure is directed toward apparatuses and methods for interacting a first liquid and a second liquid in one or more fluidic channels. Such apparatuses and methods can involve a capillary barrier that positions a meniscus of the first liquid at a fluid-interface region using capillary forces. Additionally, an escape path or channel for the second liquid permits flow of the second liquid toward the fluid-interface region, where a path is provided for fluid to exit. Further, some form of a fluid-flow limiter is provided as means for limiting volume flow rate of escaping fluid.

Certain other embodiments of the present disclosure are directed towards apparatuses and methods for interacting a first liquid and a second liquid in a capillary structure having a fluid-interface region. Such methods include providing a capillary structure that includes a first microfluidic channel for guiding the first liquid toward the fluid-interface region and a second microfluidic channel for guiding the second liquid toward the fluid-interface region. The fluid-interface region has a capillary barrier to arrest flow of the first liquid flowing toward the fluid-interface region at a nominal fluid pressure along the first microfluidic channel. Additionally, these methods involve causing the first liquid to flow in the first microfluidic channel until a state in which the capillary barrier has arrested flow of the first liquid in the first microfluidic channel. While in the state in which the capillary barrier has arrested flow of the first liquid in the first microfluidic channel, gas pressure is released from the fluid-interface region via a gas-outflow port. This release occurs due to and while the second liquid is flowing in the second microfluidic channel toward the fluid-interface region.

Consistent with many of the above aspects, examples of related apparatuses include a capillary structure having a first microfluidic channel for guiding a first liquid toward a fluid-interface region and a second microfluidic channel for guiding a second liquid toward the fluid-interface region. The fluid-interface region includes a capillary barrier that arrests the first liquid flowing toward the fluid-interface region at a nominal fluid pressure along the first microfluidic channel. This type of apparatus can also include a gas-outflow port, constructed to reduce or prevent a loss of fluid, that releases gas pressure in the fluid-interface region. This port is useful during a state in which the capillary barrier has arrested flow of the first liquid in the first microfluidic channel, and in which the second liquid flows in the second microfluidic channel toward the fluid-interface region.

The above discussion/summary is not intended to describe each embodiment or every implementation of the present disclosure. The figures and detailed description that follow also exemplify various embodiments.

FIGURES

Various example embodiments may be more completely understood in consideration of the following detailed description in connection with the accompanying drawings, in which:

FIG. 2B shows an example capillary structure including a first liquid arrested, and a second liquid flowing towards a fluid-interface region, consistent with various aspects of the present disclosure.

While the disclosure is amenable to various modifications and alternative forms, specifics thereof have been shown by way of example in the drawings and will be described in detail. It should be understood, however, that the disclosure is not limited only to the particular embodiments described. On the contrary, the disclosure is to cover all modifications, equivalents, and alternatives falling within the scope of the disclosure including aspects defined in the claims. In addition, the term "example" as used throughout this application is only by way of illustration, and not limitation.

DESCRIPTION

Aspects of the present disclosure are believed to be applicable to a variety of different types of devices, systems and arrangements involving the creation of fluid-to-fluid interfaces via capillary barriers in order to stop advancing liquids at the interface points. The capillary barriers, consistent with various aspects of the present disclosure, utilize surface forces to hold or pin the liquid meniscus of a fluid in a desired and stationary location. Once the meniscus of the fluid is pinned at a junction, different liquids are loaded, and backfilled to the meniscus of the first fluid. The liquid-to-liquid interface created aids in, for example, finite injection of cell lysate for highly efficient extraction of nucleic acids by ITP. While the present disclosure is not necessarily so limited, various aspects of the disclosure may be appreciated through a discussion of examples using this context.

Various example embodiments are directed to methods and apparatus for interacting a first liquid and a second liquid in a capillary structure having a fluid-interface region. In the capillary structure, a first microfluidic channel is provided for guiding the first liquid toward the fluid-interface region, and a second microfluidic channel is provided for guiding the second liquid toward the fluid-interface region. The fluid-interface region includes a capillary barrier that arrests the flow of the first liquid as it moves toward the fluid-interface region at a nominal fluid pressure along the first microfluidic channel. The first liquid flows in the first microfluidic channel until a state in which the capillary barrier arrests the flow of the first liquid. While in the state in which the capillary barrier has arrested flow of the first liquid in the first microfluidic channel, gas pressure is released. Gas pressure is released from the fluid-interface region via a gas-outflow port (due to and) while the second liquid is flowing in the second microfluidic channel toward the fluid-interface region. In certain embodiments, after the flow of the first liquid is arrested, the second liquid flows into the second microfluidic channel until a liquid-to-liquid interface is created between the first liquid and the second liquid.

Various aspects of the present disclosure are provided to allow liquid interfaces created in microfluidic channels without loss of sample liquid. Such apparatuses and methods can involve a capillary barrier that positions a meniscus of the first liquid at a fluid-interface region using capillary forces, while using an escape path to permit flow of the second liquid toward the fluid-interface region. A fluid-flow limiter, e.g., located within the escape path, is provided as a mechanism for limiting volume flow rate of escaping fluid. As exemplified throughout and specifically illustrated with FIG. 4, different structures can be used to implement this function of limiting volume flow rate of (escaping) fluid. Examples include a low volume channel, a constricted channel, abrupt changes along the path, a passive valve, an active valve, an orifice, a ramp or post structure, and/or a constriction in the channel hydraulic diameter that is used to increase hydraulic resistance.

In certain other embodiments, a microfluidic chip is provided to support the capillary structure. A protrusion can be included, e.g., in the form of a post, near or at an upstream portion of the fluid-interface region and on a wall of the path for the first liquid to flow toward the fluid-interface region; the protrusion is configured and arranged for limiting by presenting a force to oppose the volume flow rate of the (second) liquid. The microfluidic chip also includes circuitry that receives data indicative of an interaction between the first liquid and the second liquid. In certain other embodiments, consistent with various aspects of the present disclosure, a first fluid introduction port is provided on the microfluidic chip to present the first fluid to the first microfluidic channel, and a second fluid introduction port is provided on the microfluidic chip to present the second fluid to the second microfluidic channel.

One or more of the first microfluidic channel and the second microfluidic channel, in certain embodiments of the present disclosure, respectively include hydrophobic surfaces in order to assist in arresting the liquid flow in the fluid-interface region. In certain embodiments, the first microfluidic channel and the second microfluidic channel are formed from polydimethylsiloxane (PDMS). Additionally, in certain embodiments of the present disclosure, the upstream portion of the capillary barrier is at least in part defined by a change in a cross-sectional area for the first liquid flowing in the capillary structure. In these embodiments, cross-sectional area change is sufficient to arrest the first liquid flow in the fluid-interface region. Further, in these embodiments, the capillary barrier assists in arresting the first liquid when it is flowing in the first microfluidic channel. Additionally, in other embodiments of the present disclosure, surface forces arresting fluid flow in the first microfluidic channel is approximately equal to surface forces arresting fluid flow in the capillary barrier. In this manner, the capillary barrier at the upstream portion of the capillary barrier is defined by a change in cross-sectional area for the first liquid flowing in the capillary structure, which assists in arresting of the first liquid when it is flowing in the first microfluidic channel. In certain embodiments of the present disclosure, an intersection of the first microfluidic channel and the second microfluidic channel form a junction. Various embodiments of the present disclosure load the first fluid and the second fluid without using a vacuum.

In certain embodiments of the present disclosure, at least one of the first fluid and the second fluid is a fluid that includes DNA, RNA, proteins and/or cells. Additionally, certain embodiments of the present disclosure also include a microfluidic chip that supports the capillary structure and circuitry that receives data indicative of an interaction between the first liquid and the second liquid. In various embodiments, the circuitry performs microfluidics analysis of quantification and quality control of DNA, RNA, proteins and/or cells that are present in the first fluid or the second fluid. Additionally, in other embodiments, the circuitry on the microfluidic chip performs preparative electrophoresis analysis of separation and extraction of DNA fragments present in the first fluid or the second fluid. In other embodiments, circuitry analyzes target nucleic acid enrichment in at least one of the first fluid and the second fluid. The circuitry, in other embodiments, is provided to perform genetic analysis of aspects of the first fluid or the second fluid based on the polymerase chain reaction. As illustrated by the various embodiments and applications of circuitry, the capillary structure, as arranged on a microfluidic chip, is useful to numerous different applications.

The capillary structure is compatible with various systems and apparatus that analyze and/or process the interactions between two liquids. Further, embodiments of the capillary structure arranged on the microfluidic chip and having circuitry that analyzes quantification and quality control of DNA, RNA, proteins and/or cells is compatible with various apparatus and systems such as, for example, Qiagen's Qiaxcel; Agilent Bioanalyzer; Bio-Rad's Experion; Shimadzu—MCE-202 MultiNA; and Perkin Elmer's LabChip GX II. Additionally, embodiments of the capillary structure arranged on the microfluidic chip and having circuitry that performs preparative electrophoresis analysis of separation and extraction of DNA fragments is compatible with various apparatus and systems such as, for example, Sage Science's Pippin Prep and BluePippen Prep; and Perkin Elmer's Labchip XT. Further, embodiments of the capillary structure arranged on the microfluidic chip and having circuitry that analyzes target nucleic acid enrichment is compatible with various apparatus and systems such as, for example, Fluidigm's Access Array. The capillary structure is also useful in loading of reagents and/or sample volumes as would occur in microfluidic thermocylers (e.g., Qiagen's LabDisk Player).

Figure 1:
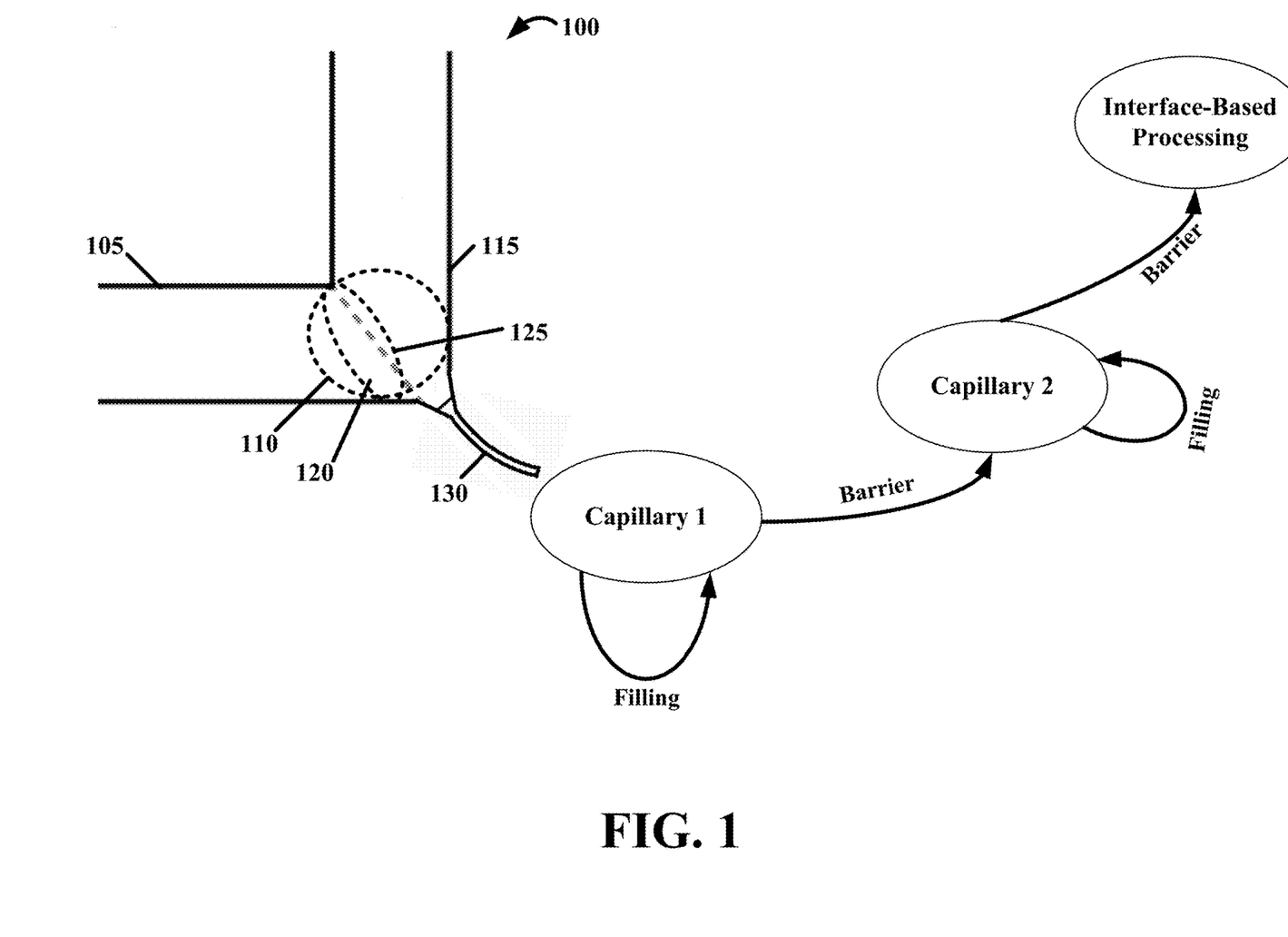
FIG. 1 shows an example capillary structure and state diagram, consistent with various aspects of the present disclosure.

Turning now to the Figures, FIG. 1 shows an example capillary structure and state diagram, consistent with various aspects of the present disclosure. FIG. 1 shows a capillary structure 100 including a first microfluidic channel 105 and a second microfluidic channel 115. The first microfluidic channel 105 is provided for guiding a first liquid toward a fluid-interface region 110, and the second microfluidic channel 115 is provided for guiding a second liquid toward the fluid-interface region 110. The fluid-interface region 110 includes a capillary barrier 120 that arrests the flow of the first liquid in response to the first liquid flowing toward the fluid-interface region 110 at a nominal fluid pressure. An upstream portion of the capillary barrier 120 provides a meniscus barrier 125 for the first liquid. The first liquid flows in the first microfluidic channel 105 until a state in which the capillary barrier 120 arrests the flow. While in this state, gas pressure may be released from the fluid-interface region 110 via a fluid-gas-outflow port 130, while the second liquid is flowing in the second microfluidic channel 115 toward the fluid-interface region 110.

As shown in the state diagram of FIG. 1, after the first liquid hits the meniscus barrier, the second microfluidic channel 115 is filled with the second liquid until the second liquid contacts the first liquid at the meniscus barrier. At this stage, the wetting between the first and second liquids can lead to fluid loss via the gas-outflow port 130, which is designed to limit (by presenting an opposing force relative to) the volume flow rate of the (second) fluid by blocking or reducing fluid flow through a path that permits gas to outflow. Interface-based analysis is then performed at the interface of the first liquid and the second liquid.

Figures 2A, 2C:
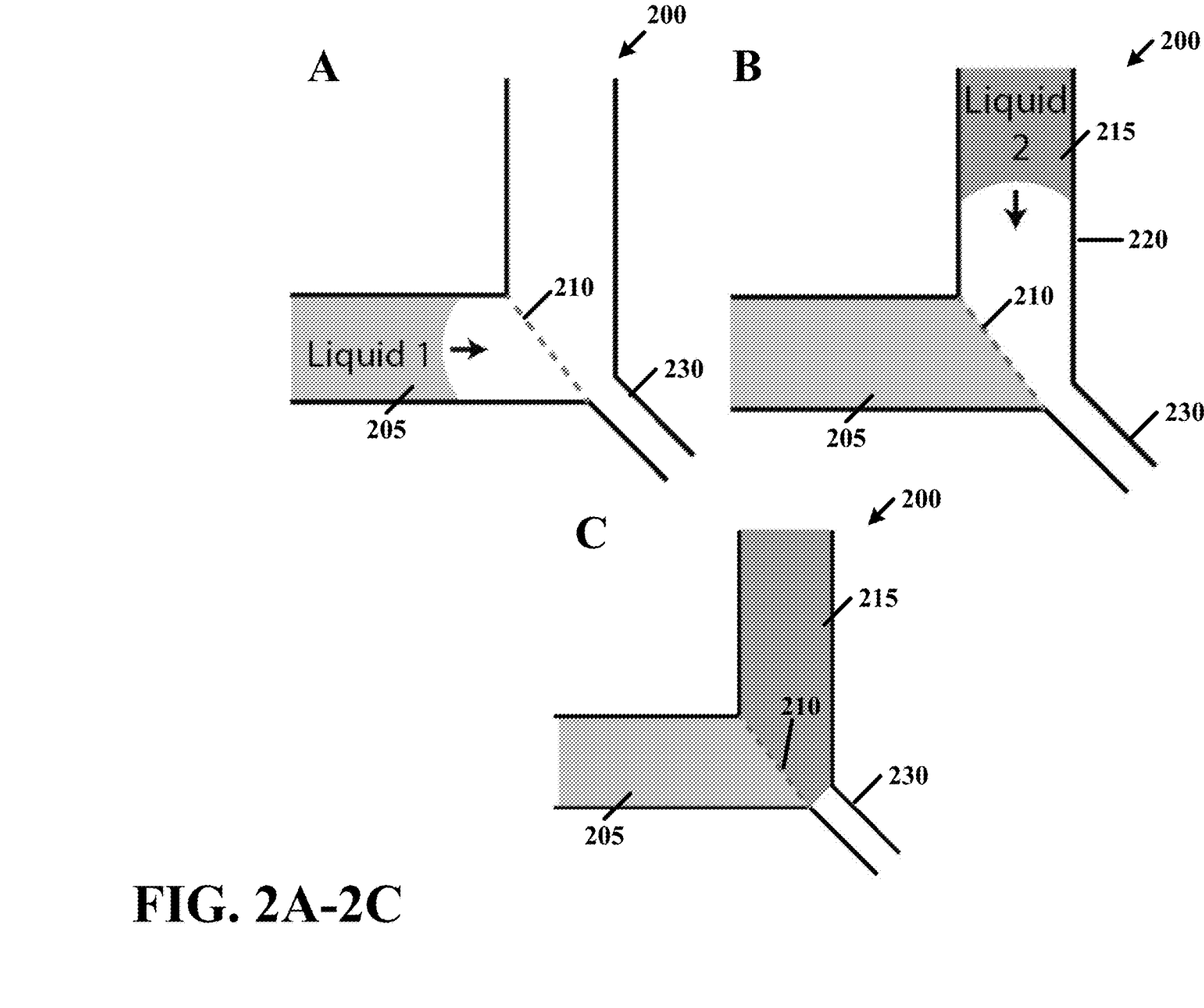
FIG. 2A shows an example capillary structure including a first liquid flowing towards a fluid-interface region, consistent with various aspects of the present disclosure.
FIG. 2C shows a liquid-to-liquid interface of a first liquid and a second liquid in a capillary structure, consistent with various aspects of the present disclosure.

FIGS. 2A-2D show exemplary capillary structures, consistent with various aspects of the present disclosure. FIG. 2A shows one such capillary structure 200 including a first liquid 205 flowing in a microfluidic channel. The fluid flow stops at a barrier 210 as indicated by dashed lines in FIG. 2B which show the capillary structure 200 including a first liquid 205 arrested and a second liquid 215 flowing in a second channel 220 of the capillary structure 200. The second liquid 215 flows up to and until a liquid-to-liquid interface is created at the point (or barrier 210) where the first liquid was arrested. The liquid-to-liquid interface is shown separating at the liquid barrier 210 in FIG. 2C. Common to each of FIGS. 2A, 2B and 2C is out flow port 230 (denoted to relate to port 130 of FIG. 1).

Figure 2D:
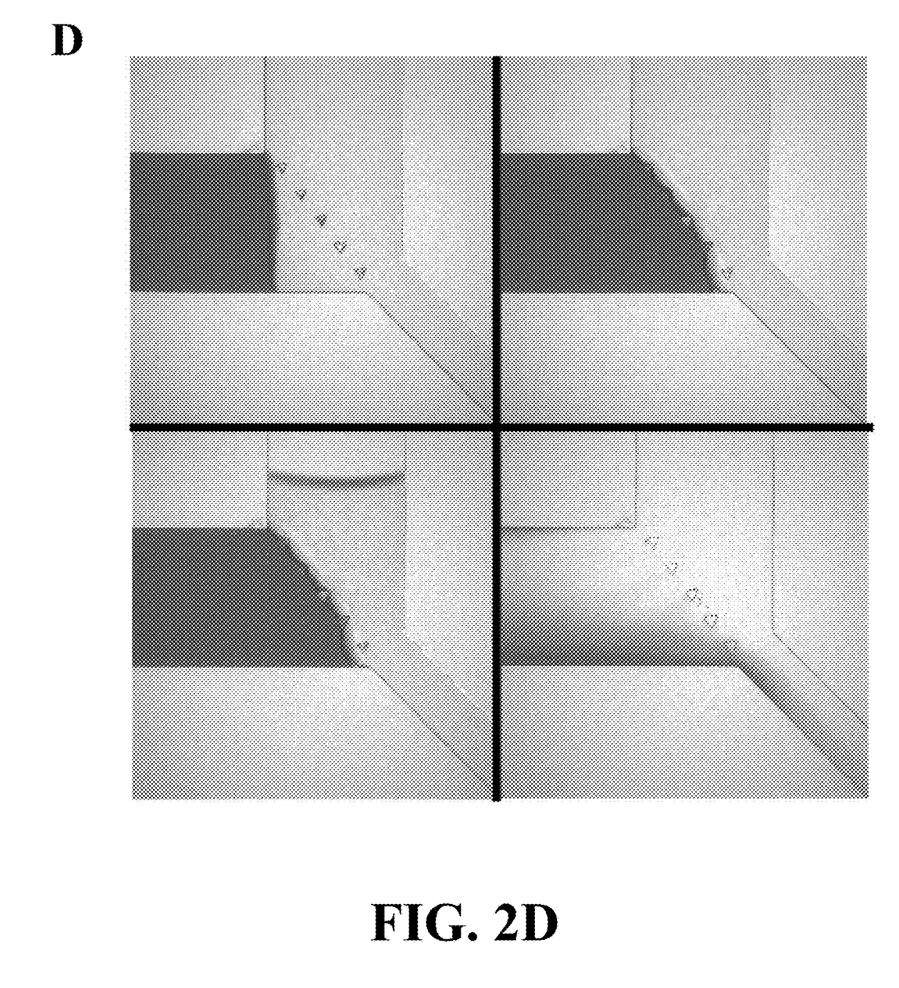
FIG. 2D shows example images of a first liquid and a second liquid in a capillary structure, consistent with various aspects of the present disclosure.

FIG. 2D shows example images of a similarly constructed capillary structure, consistent with various aspects of the present disclosure, where in the first liquid is blood lysate, and the second liquid is electrophoresis buffer. Additionally, the capillary structure in which the liquids are loaded is a polydimethylsiloxane (PDMS) chip. As is shown in the upper left corner of FIG. 2D, blood lysate is loaded from the left by applying a vacuum at the bottom right portion of the chip. The upper right portion of FIG. 2D shows the lysate pinned at the barrier. The lower left portion of FIG. 2D shows the leading electrolyte (the electrophoresis buffer) for ITP loaded from the top capillary. A sharp interface of the electrolyte and the blood lysate volume is then formed. The lower right portion of FIG. 2D shows a snapshot at the point in which the lysate and leading electrolyte meet. After these liquids meet, pressure-driven flow will occur and disrupt the interface. However, due to the design of the chip, consistent with various aspects of the present disclosure, the blood lysate volume is wasted by flowing into an outlet waste channel.

Figure 3A:
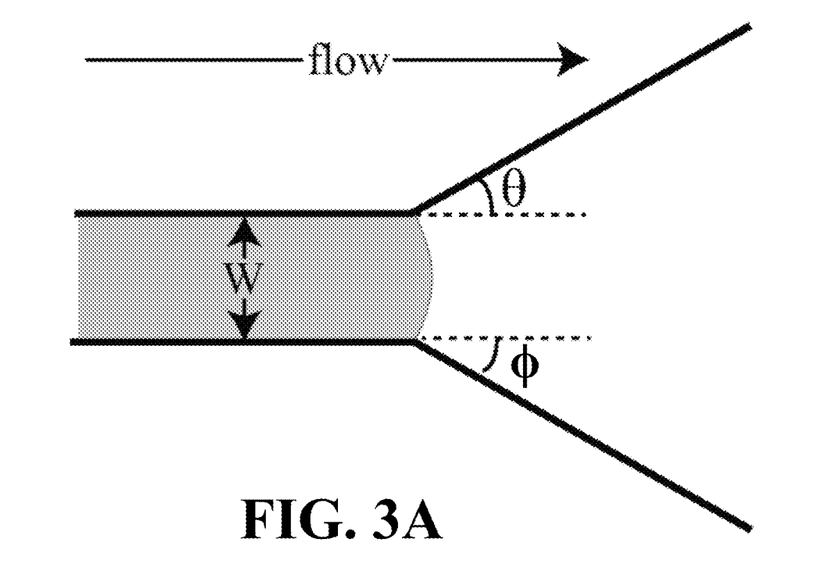
FIG. 3A shows a first example capillary barrier, consistent with various aspects of the present disclosure.

FIG. 3 shows example capillary barriers, consistent with various aspects of the present disclosure. For instance, FIG. 3A shows a first example capillary barrier. In FIG. 3A, a capillary barrier is created based on an advancing liquid contact line (advancing into a region occupied by some gas) encountering a liquid capillary or chamber geometry. The capillary forces arrest the motion of the liquid, and form a stationary liquid front even in the presence of applied pressure differences between the liquid and gas sides. As can be seen in FIG. 3A, fluid-flow is arrested due to surface forces at the upstream portion of capillary based on a change in cross-sectional area, which is shown based on the representative angle differences ($\phi$ and $\Phi$) between the upstream portion of the capillary and the downstream portion of the capillary. In certain embodiments, $\phi$ and $\Phi$ are equal, and in other embodiments $\phi$ and $\Phi$ are unequal.

Figure 3B:
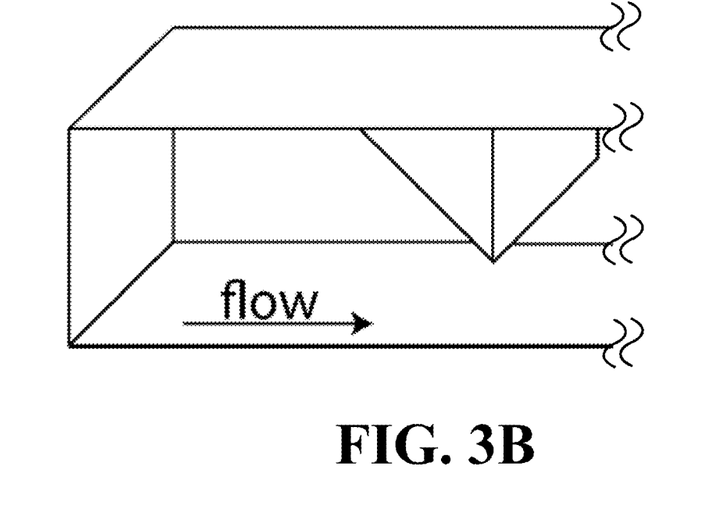
FIG. 3B shows a second example capillary barrier, consistent with various aspects of the present disclosure.

FIG. 3B shows a second example fluid-flow capillary barrier, consistent with various aspects of the present disclosure. The capillary barrier shown in FIG. 3B is the result of a series of posts inside the capillary. The structures allow for fabrication with high resolution, but without the ability to make fully 3-dimensional structures. For example, polydimethylsiloxane (PDMS) poured on a SU-8 mask can easily be used to create posts with sharp edges, but the capillaries are limited to a single mask thickness. In the embodiment shown in FIG. 3B, the capillary barrier includes a series of small (e.g., 120 µm in length) triangular posts situated along the capillary. As a first liquid flows into the device along one capillary, and it becomes pinned at the capillary barrier, thereby forming a meniscus. This meniscus remains stationary as a second fluid (e.g., electrophoresis buffer) is filled from the connecting capillary (not shown), and air escapes through a narrow side-channel (e.g., as shown in FIG. 1). As a liquid reaches the capillary barriers, the first liquid comes into contact with the second liquid. The capillary barrier structure shown in FIG. 3B is a ramp structure. In other embodiments, ramp structures are used to create capillary barriers inside of the capillary channels.

Such a ramp structure can be implemented and manufactured using thermoplastic molding, where the 3D molds are machined. The capillary barrier structure decreases the effective channel dimensions, and then allows expansion. The liquid meniscus is stopped by the increase in surface area needed to cross the expansion.

Figure 4:
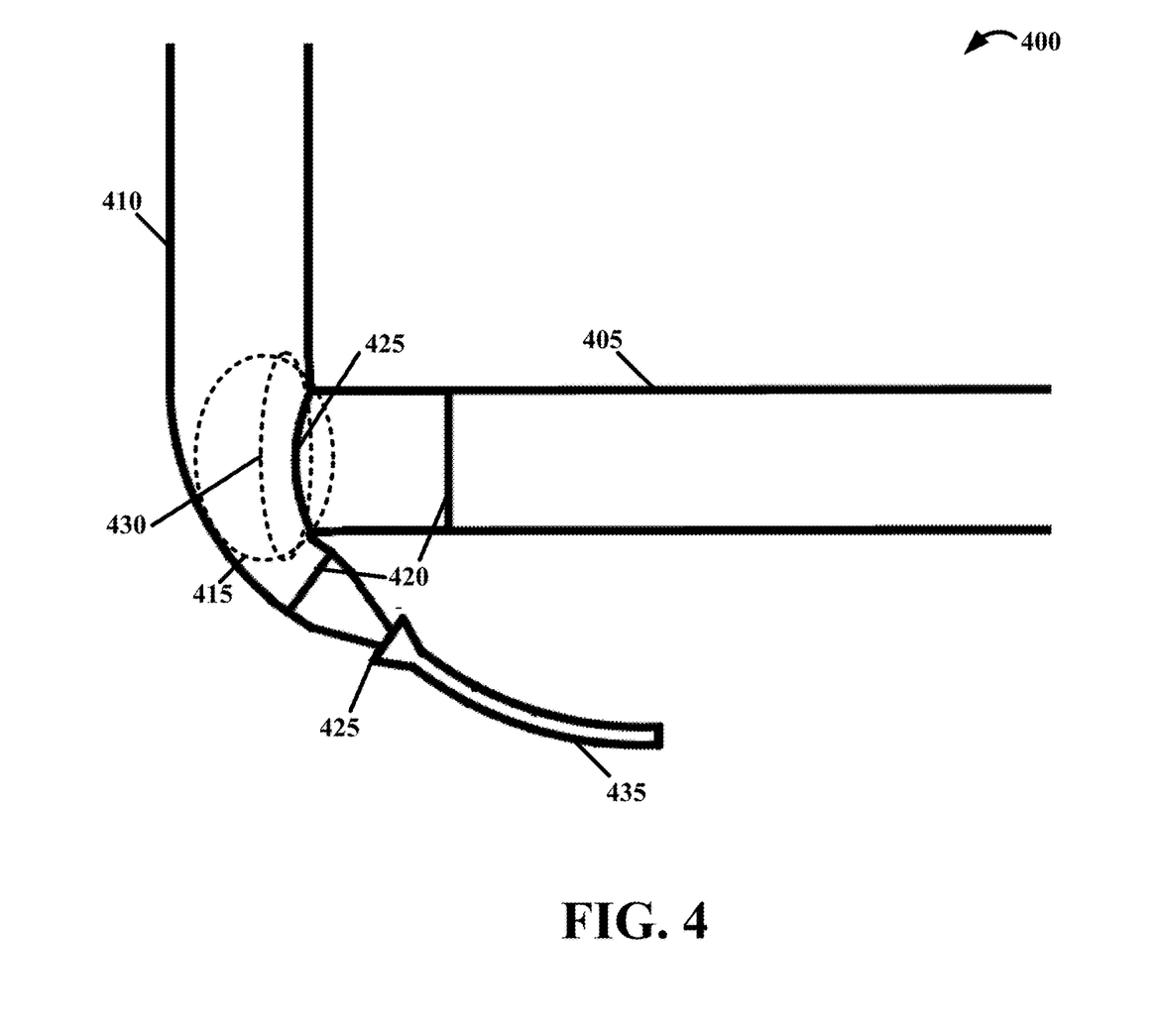
FIG. 4 shows an example capillary structure, consistent with various aspects of the present disclosure.

FIG. 4 shows an example capillary structure consistent with various aspects of the present disclosure. The capillary structure 400 in FIG. 4 includes a first microfluidic channel 405 and a second microfluidic channel 410. The first microfluidic channel 405 is provided for guiding a first liquid toward a fluid-interface region 415, and the second microfluidic channel 410 is provided for guiding a second liquid toward the fluid-interface region 415. The first microfluidic channel 405 and the second microfluidic channel 410 include respective barrier structures 420 and respective expansions (or expansion regions) 425 in the capillaries thereafter. These barrier structures 420 and expansions 425 assist in creating a capillary barrier 430 that arrests flow of the first liquid in response to the first liquid flowing toward the fluid-interface region 415 (at a nominal fluid pressure). An upstream portion of the capillary barrier 430 provides a meniscus barrier, for example, at the expansion 425 in the first microfluidic channel 405. The first liquid flows in the first microfluidic channel 405 until a state in which the capillary barrier 430 arrests the flow of the first liquid at least in part based on the barrier structures 420, and expansions 425. While in the state in which the capillary barrier 430 has arrested flow of the first liquid in the first microfluidic channel 405, gas pressure is released, via a gas-outflow port 435, from the fluid-interface region 415 while the second liquid is flowing in the second microfluidic channel 410 toward the fluid-interface region 415. The barrier structure 420 and the expansion 425 are arranged near the second microfluidic channel 410 to mitigate loss of liquids via the gas-outflow port 435. As illustrated, the gas-outflow port 435 has a constricted volume area (per illustrated abrupt changes in channel dimensions) so as to provide a passive means by which fluid loss would occur.

Certain aspects of the present disclosure are directed toward use of microfluidic chips for nucleic acid isolation using ITP. Glass, plastic, or injection-molded plastic microfluidic chips can be used for ITP purification. Such microfluidic chips, for example, can achieve high extraction efficiencies of nucleic acids through processing 25 µL of blood lysate. The recovery efficiency, in certain embodiments, is based at least in-part on providing a separation channel volume that is on the order of the sample volume, and the use reservoirs containing buffering solutions free of sample for electrolysis. More specifically, a high volume separation can be achieved, in certain embodiments, with a 2 mm×0.15 mm×100 mm separation channel which maintains sufficient heat rejection to avoid unwanted effects of Joule heating. The electrodes are placed on dedicated buffering reservoirs, which are free of sample and contain high local buffer concentration. These reservoirs are effective in buffering the pH caused by electrolysis, even when large volumes are processed. In these specific embodiments, the sample channel has with a total volume of 25 µL, and the separation channel has a total volume of 30 µL. Additionally, the reservoirs, with access to the fluidic channel, each can hold a total volume of 70 µL. Each reservoir can be compatible with Leur lock connectors. Further, the microfluidic chips can be made from poly-methyl methacrylate (PMMA), Topas, a cyclic olefin copolymer (COC), or a similar material, and sealed with plastic films with a thickness of 140 µm (COC) or 175 µm (PMMA). COC has a reported equilibrium water contact angle of around 97°, while the PMMA is more hydrophilic, with a reported water contact angle of 60°.

Figure 5:
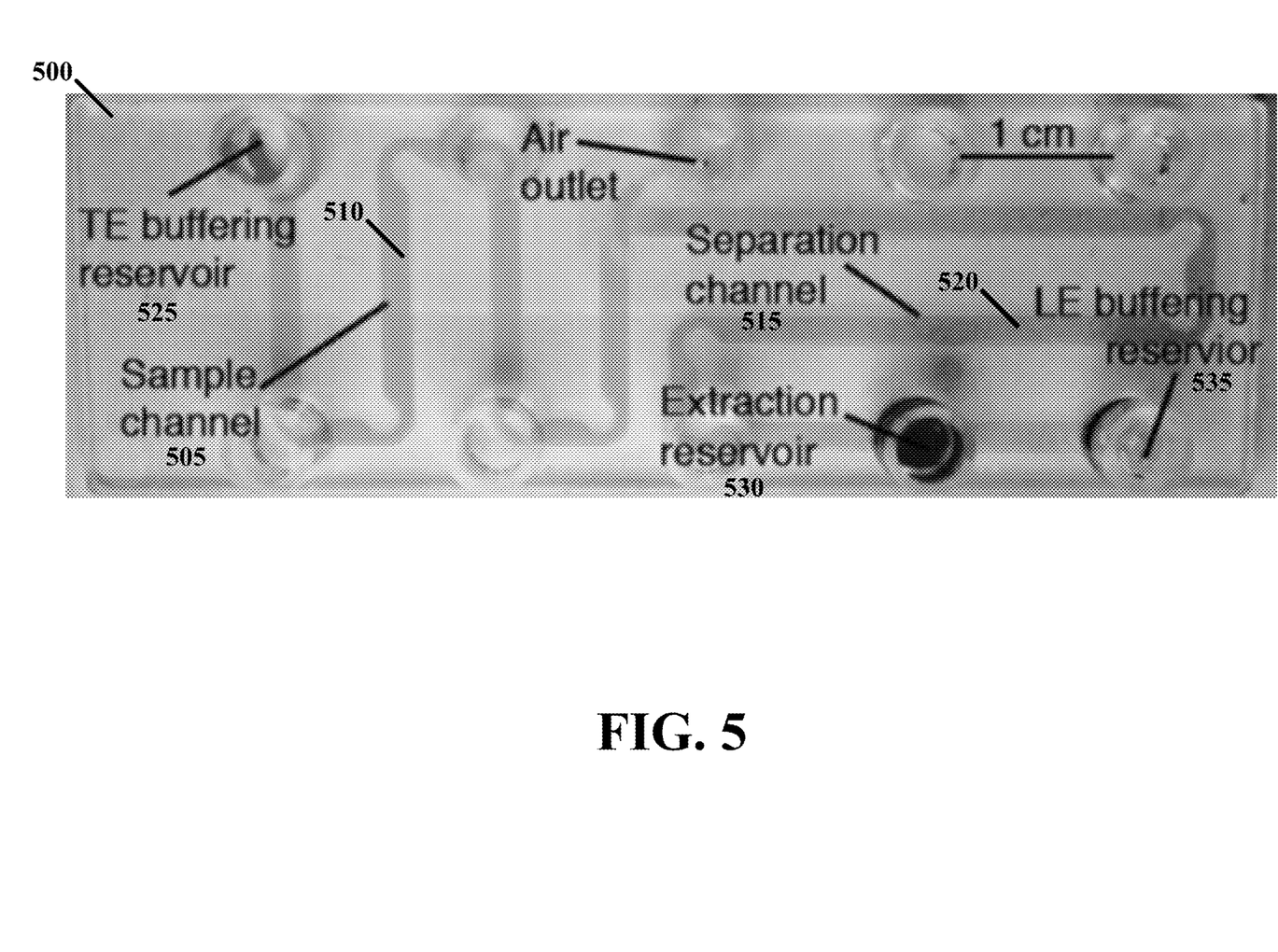
FIG. 5 shows an example microfluidic chip arrangement, consistent with various aspects of the present disclosure.

FIG. 5 shows an example microfluidic chip arrangement 500, consistent with various aspects of the present disclosure. Each of the channels in the microfluidic chip arrangement 500 are loaded with water having different dyes. A sample channel 505 has a first fluid 510, while a separation channel 515 has a second fluid 520. A more detailed view of the junction between these two channels and the structure of the connected air outlet channel is shown FIG. 6. The displayed trailing electrolyte (TE) buffering reservoir 525, sample extraction reservoir 530, and LE buffering reservoir 535 are used and connected to the channels (as is shown in further detail in FIG. 7). Each channel corner in the device is an optimized 90° turn to minimize electrokinetic dispersion due non-uniform electric fields in the turn. These turns have a constriction ratio of 0.5 and a recovery ratio of 1.0

The reservoirs (525, 530, 535) in the device are arranged so that the two electrode-containing reservoirs (525 and 535) have a high buffering capacity without affecting the chemistry of a sample or extracted nucleic acids. To achieve this, a sample is loaded directly into the sample channel 505, and not into the TE buffering reservoir 525. Further, the LE buffering reservoir 535 is separate from the sample extraction reservoir 530, and connected to the latter by a short channel.

Loading structures at the junction between the sample and separation channels can allow creation of a sharp interface between the sample and the LE solutions. These structures also enable loading of the sample into the device without wasting liquid into a vacuum port. Ramps and a sudden expansion in channel height can be used to achieve capillary barriers. More specifically, the ramps reduce the height of the channel from 150 µm to 75 µm over a distance of about 2 mm along the channel. This ramp can rise from the bottom wall of the channel and terminate in a sharp step in channel height back to 150 µm. Liquid wicking up to this structure faces an energetic barrier associated with expanding past the ramp (as additional liquid surface area is required for the liquid to advance). These valve structures can be oriented so that the liquid stopped by the capillary barrier can be wetted by liquid from an adjacent channel, creating a bubble-free liquid-to-liquid interface. As shown and discussed in further detail in FIG. 2, capillary barriers can be used to provide a sample-to-separation buffer interface, and also to provide a final fluid stop at a connected vacuum outlet channel.

Figure 6:
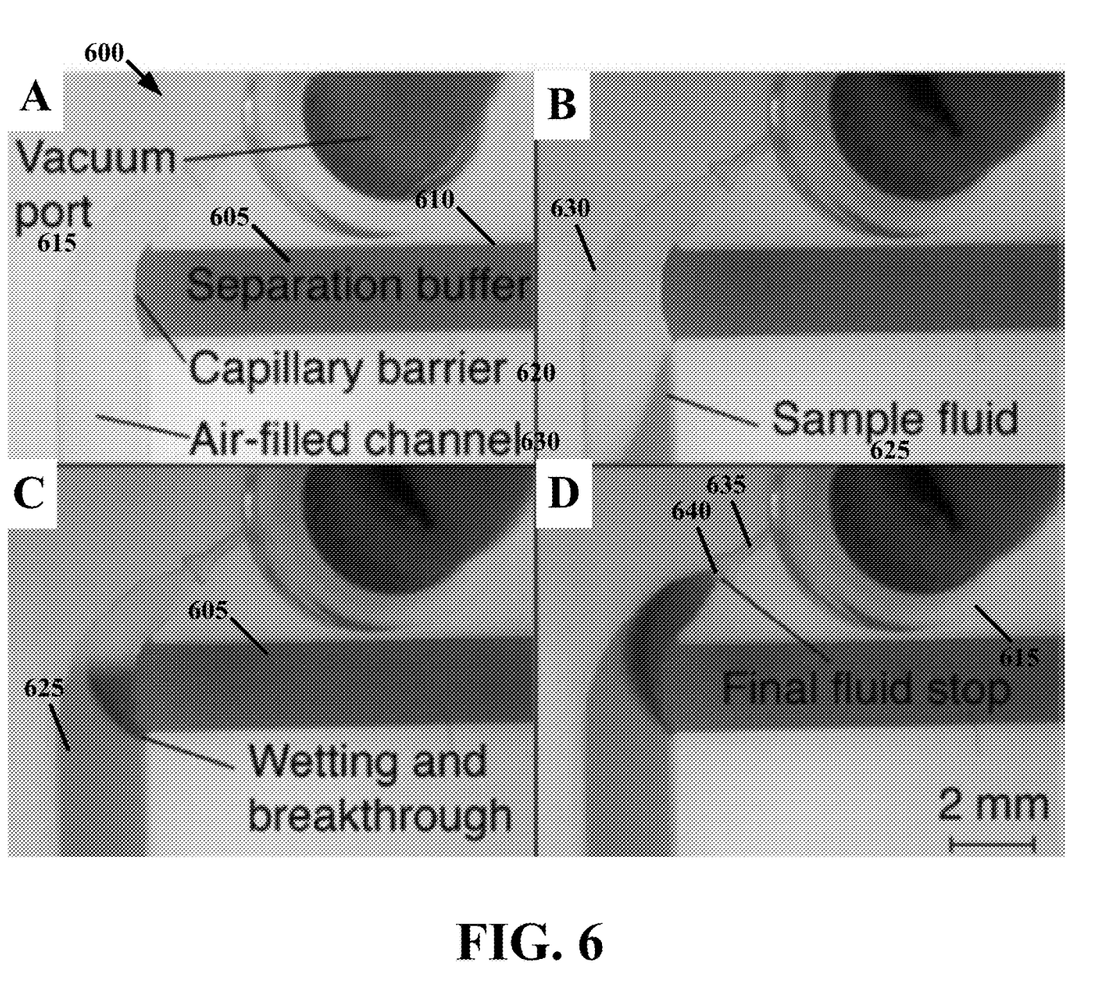
FIG. 6 shows stages in an example capillary-barrier-aided loading of a microfluidic chip arrangement, consistent with various aspects of the present disclosure.

FIG. 6 shows stages in an example capillary-barrier-aided loading of a microfluidic chip arrangement 600, consistent with various aspects of the present disclosure. As shown in FIG. 6A, a first liquid 605, simulating a separation buffer, is initially loaded into a separation channel 610. A −0.1 psig vacuum is applied at a vacuum port 615, and the first liquid 605, a simulated separation buffer, flows to a capillary barrier 620, where it stops at the precise edge of the expansion downstream of the capillary barrier 620. As shown in FIG. 6B, a second liquid 625, simulating a sample solution, enters through a sample channel 630. As shown in FIG. 6C, the second liquid 625, the simulated sample solution, forms a liquid-to-liquid interface (repeatedly free of bubbles) with the first liquid 605, the simulated separation buffer. The two liquid volumes then flow in parallel toward an air outlet 635. As shown in FIG. 6D, the volume near the liquid-to-liquid interface is run up against and stopped by a fluid-flow limiter 640 inside the vacuum port 615. This avoids wasting either liquid into the vacuum. A sharp interface is preserved between the two liquid zones and the ITP process is ready to begin. The fluid-flow limiter 640 can be a ramp or post structure, consistent with various aspects of the present disclosure, a low volume channel, a constricted channel, abrupt changes along the way, a passive valve, an active valve, an orifice, a ramp, and/or a constriction in the channel hydraulic diameter that is used to increase hydraulic resistance.

Figure 7:
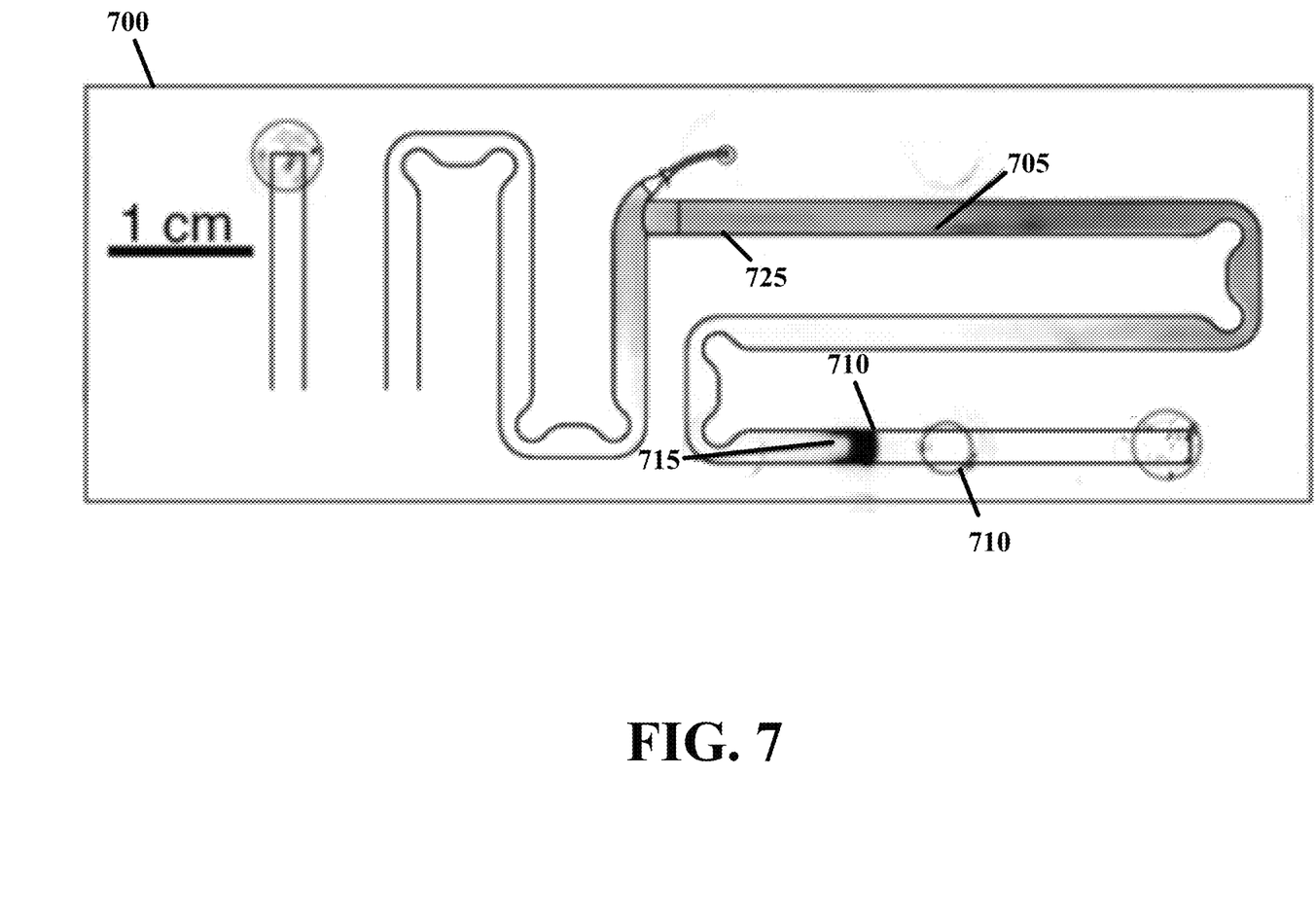
FIG. 7 depicts an example showing separation between two liquids on a microfluidic chip arrangement, consistent with various aspects of the present disclosure.

FIG. 7 depicts an example showing separation between two liquids on a microfluidic chip arrangement 700, consistent with various aspects of the present disclosure. A first fluid 705 is shown electromigrating in a long zone well behind an ITP interface 710. A second fluid 715 is shown collected at the ITP interface 710. The second fluid 715 is focused in a zone and is about to elute into an extraction reservoir 720, allowing it to be selectively collected. The first fluid 705 remains behind, unfocused and distributed throughout a large portion of a separation channel 725.

In certain embodiments, a LE buffering reservoir has a separation capacity of approximately 173 mC (charge processed), and the sample has a separation parameter (charge required to completely process sample) of 24 mC. The separation capacity is greater than the separation parameter, and so the fluid that is to be collected at the ITP interface can be collected with high efficiency (prior to its arrival at the extraction well). The separation can be performed at 100 µA.

Experimental and/or More Detailed Example Embodiments

Figure 8:
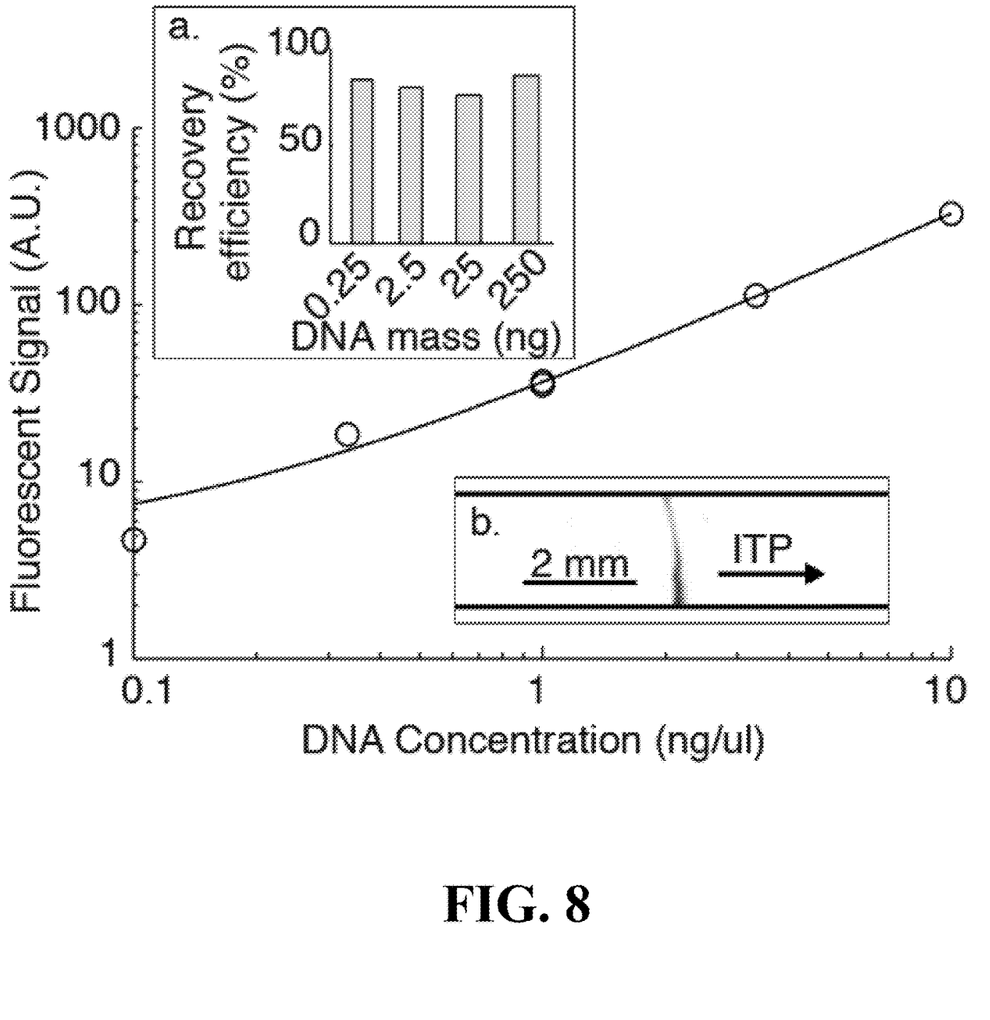
FIG. 8 shows an example fluorescence quantification of DNA, consistent with various aspects of the present disclosure.

FIG. 8 shows an example fluorescence quantification of DNA, consistent with various aspects of the present disclosure. FIG. 8 shows an experimental embodiment that was used to determine the fluorescence quantification of DNA; a channel was filled with known concentrations of DNA suspended in a LE buffering reservoir. A calibration curve was established relating the fluorescent signal collected by a charge coupling device (CCD) camera to DNA concentration. ITP was performed from samples of the DNA of known concentrations suspended in LE. A microfluidic channel arrangement, consistent with various aspects of the present disclosure, was used with a separation parameter of 55 mC and a separation capacity of 159 mC, so that the processing efficiency was not limited by the flux of nucleic acid to the ITP interface. A set of 10 images of the ITP zone was taken near an extraction reservoir, and the average integrated fluorescent signal of the zone in these images was used to quantify the total DNA amount. The DNA recovery was computed using the DNA calibration curve. As shown in FIG. 5, the recovery efficiency is consistently 76-86%, for the entire 250 pg to 250 ng of DNA range explored. The inset portion of FIG. 8 shows a representative image of DNA focused on the ITP interface and electromigrating through the device. This DNA band is approximately 8 mm from the extraction reservoir.

In another example experimental embodiment, DNA is extracted from whole human blood samples using a microfluidic channel arrangement, consistent with various aspects of the present disclosure. While nucleic acid purification from blood samples has been shown, the results have so far been complicated by the dilution factor of the extracted sample into the qPCR reaction. For example, typical previous ITP extraction studies have diluted blood samples 103 to 104-fold as the liquid is dispensed into the PCR reaction. The latter dilution also dilutes inhibitors, and so it becomes interesting to test less aggressive dilutions of the extracted DNA. In this example, blood was diluted 10× when preparing the blood lysate. DNA from the 25 µL blood lysate sample was then extracted via ITP and eluted into the 25 µL volume of our chip's extraction reservoir. Therefore, both the chip and extraction processes contribute to no change of lysate sample volume (no dilution). After extraction, the DNA sample was diluted 10× into the PCR master mix. The total dilution factor of the entire process (the lysing, extraction and PCR solution preparation) was 100×, more directly showing the power of ITP as a purification method.

Figure 9:
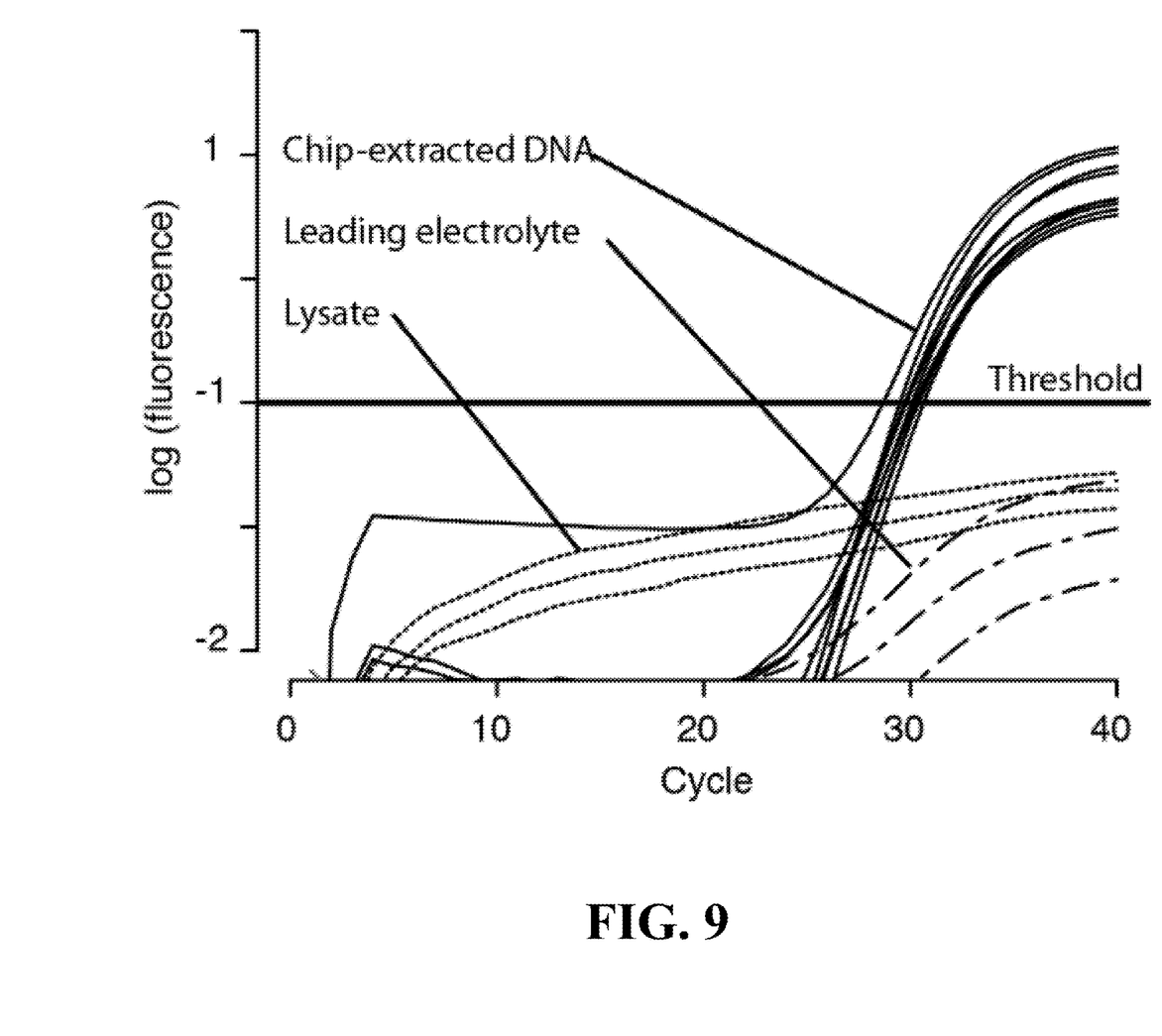
FIG. 9 shows an example quantitative polymerase chain reaction (qPCR) analysis of DNA purified from whole human blood using ITP on a microfluidic channel arrangement, consistent with various aspects of the present disclosure.

FIG. 9 shows an example qPCR analysis of DNA purified from whole human blood using ITP on a microfluidic channel arrangement, consistent with various aspects of the present disclosure. qPCR analysis of DNA purified from whole human blood using ITP on the new microfluidic device. DNA extracted using ITP, and control samples were amplified in the presence of a primer for the human gene BRAC2. The log of fluorescent signals versus cycle number is plotted. The negative control samples, (template-free LE buffer and unprocessed blood lysate) have fluorescent signals that remain below the threshold, indicating negligible PCR amplification. DNA extracted from blood using ITP amplifies leading to fluorescence well above threshold. The melting temperature of the amplicon (not shown) from all amplified samples was 74° C. This temperature matches approximate theoretical predictions from the Promega amplicon melting tool.

Various aspects of the present disclosure are directed toward capillary barriers that control fluid flow, without the use of a vacuum, by utilizing surface hydrophobicity of a microfluidic channel, and/or abrupt changes in channel dimension to create capillary valves to halt flow. As an advancing liquid enters a region of the channel which expands to a wider cross-section, the surface area of the liquid-air interface increases to allow for the liquid to continue advancing. This expanded surface area results in a force that limits volume flow rate (by way of a force that opposes the flow of the liquid). If the surface expansion is large enough, the liquid will stop advancing. Various embodiments of the present disclosure also form capillary barriers based on regions of hydrophobic surfaces, barriers such as one or more ramps or posts in the channel configured and arranged for presenting a force to oppose the flow of the liquid, and/or other methods of achieving sudden expansions in microfluidic capillaries with sudden contractions in microfluidic capillaries.

To perform fluorescence quantification of extraction efficiency on microfluidic channel arrangements, consistent with various aspects of the present disclosure, an idealized chemistry can be used with samples composed of salmon sperm DNA diluted in buffer. To create the calibration curves, the sodium salt of salmon sperm DNA was diluted (Sigma Aldrich, St. Louis, MO) in an aqueous buffer composed of 20 mM Tris, 10 mM Hepes, with 1×SYBR® Green I (Invitrogen, CA), pH=8.2. DNA concentrations ranging from 100 pg/µL to 10 ng/µL were used. To perform ITP with these same samples, an LE composed of 100 mM Tris, 50 mM hydrochloric acid (HCl), and 1×SYBR® Green I, pH=8.2 was prepared. A buffering leading electrolyte (BLE) with 500 mM Tris, 250 mM HCl, and 25% w/v Pluronic F-127 was used. The buffering trailing electrolyte (BTE) was composed of 500 mM Tris, 250 mM HEPES, and 25% w/v Pluronic F-127. The Pluronic F-127 in both the BLE and BTE acted as a temperature-sensitive gel that acts as a liquid at 0° C. and a solid at 25° C. This helped stabilize the device to pressure driven flow. As such, we placed both the BLE and BTE on ice until they were pipetted onto the chip.

To perform ITP purification of blood with these devices, an LE composed of 90 mM Tris and 60 mM HCl (pH=7.9) was used. The BLE and BTE solutions are the same as used for fluorescence quantification. Blood lysate was prepared by mixing 10 µL of whole blood anticoagulated with acid-citrate-dextrose (ACD) with 190 µL lysis buffer, composed of 25 mM Tris, 17 mM HCl, and 1% Triton x-100, and proteinase K, 1×SYBR® Green, 0.1% PVP, and 40 mM dithiothreitol (DTT) (The whole blood was purchased from the Stanford Blood Center and stored frozen at −20° C. prior to use). This sample was then held at 65° C. for 10 min. The blood lysate was then placed on ice until it was pipetted onto the chip as the sample.

Experiments were also performed in which fluorescent dyes were separated in the microfluidic channel arrangements, consistent with various aspects of the present disclosure. Fluorescein (FL) and Alexa Fluor 488 (AF488) were separated, which emit fluoresce in the same wavelength region (excitation at 495 nm, emission at 519 nm), but have different mobilities at pH below 7. For these experiments, an LE composed of 70 mM ε-aminocaproic acid and 35 mM HCl with 0.1% w/v PVP (pH=4.6) was used. The sample was composed of 30 mM ε-aminocaproic acid and 15 mm ascorbic acid, 0.1% w/v PVP, 5 µM AF488, and 100 µM FL (pH=4.6). The BLE was composed of 200 mM ε-aminocaproic acid, 100 mM HCl, and 20% Pluronic F-127. The BTE was composed of 200 mM ε-aminocaproic acid, 100 mM Ascorbic acid, and 20% Pluronic F-127.

In certain embodiments, liquids are loaded onto a microfluidic channel arrangement, consistent with various aspects of the present disclosure, in a certain order. First, 50 µL LE is pipetted into the extraction reservoir. Vacuum (−0.1 psig) is applied at the buffering LE reservoir until the channel adjacent to it is filled, then 25 µL BLE solution is added to the buffering LE reservoir. A vacuum (−0.1 psig) is applied at the air outlet until the LE filled the entire separation channel (the liquid stopping at the capillary barrier). Then, the 25 µL sample is added to the buffering TE reservoir. Vacuum is again applied at the air outlet until the sample wetted the LE interface. Finally, BTE solution is immediately pipetted into the buffering TE reservoir to arrest pressure driven flow. This loaded chip is then used for ITP.

Purification can be performed, in certain more specific embodiments, by placing 2 cm platinum wire electrodes in the LE buffering reservoir and the TE buffering reservoir. A constant current of 100-250 µA is applied between these two reservoirs. The current is deactivated when the nucleic acid zone reaches the extraction reservoir.

Additionally, in certain embodiments, a DNA zone is monitored in the channel during ITP by fluorescently imaging the SYBR®-labeled DNA using a fluorescence microscope. When the ITP interface fully eluted into the extraction reservoir, the liquid is gently mixed in the reservoir (~25 µL) by pipetting, then collected it into an Eppendorf tube using the same pipettor.

For each collected sample, triplicate PCR reactions can be run. To set up each PCR reaction, 2 µL ITP-purified DNA was pipetted into a PCR tube containing 10 µL of 2× Fast SYBR® Green I master mix (Applied Biosystems, CA), and 200 nM primers (Invitrogen, CA). The primers were designed to amplify a 201 bp segment of the human BRAC2 gene. DNAse free water was used to adjust the volume of each reaction to 20 µL. Off-chip qPCR was then performed using a miniOpticon qPCR thermocycler (Bio-Rad, Hercules, CA). The reaction was performed with the following thermal profile: 20 second initial hold at 95° C. and 40 cycles composed of 3 second denaturation at 95° C. and 30 second annealing and extension at 60° C. Post-amplification melting curves were obtained between 55° C. and 85° C. using the same instrument, and negative control reactions were run using the LE and the unpurified whole blood lysate as a template.

Various aspects of the present disclosure are directed toward a microfluidic chip capable of achieving highly efficient ITP purification of nucleic acids from 25 µL biological samples. The chip can be designed by taking into account principles of ITP separation capacity, throughput, pH buffering capacity and dispersion minimization. The chip incorporates high aspect-ratio channels to improve heat dissipation, and optimized turn geometries to reduce dispersion around corners. The chip uses separate buffering reservoirs to decouple the buffering capacity of the device form the sample and extraction reservoir chemistry. The chip incorporates a capillary barrier structure to allow sequential loading of the fluids without loss of fluid into the vacuum port. These structures provide robust, repeatable loading using easily achievable vacuum levels. Lastly, the chip was designed for and fabricated in common COC and PMMA using injection molding, which shows the possibility for simple and scalable fabrication of these devices. This chip design can act as a platform for future studies of ITP purification by allowing practical sample volumes to be processed in about 20 mins., without wasting precious sample volume.

For further details regarding microfluidic chips, reference is made to U.S. Provisional Patent Application Ser. No. 61/785,255, to which this document claims priority benefit of, filed on Mar. 14, 2013; this patent document is fully incorporated herein by reference.

Based upon the above discussion and illustrations, those skilled in the art will readily recognize that various modifications and changes may be made to the present disclosure without strictly following the exemplary embodiments and applications illustrated and described herein. Such modifications do not depart from the true spirit and scope of the present disclosure, including that set forth in the following claims.

What is claimed is:

1. An apparatus, comprising:
    (a) a structure comprising:
        (i) a first microfluidic channel to guide a first liquid toward a fluid-interface region;
        (ii) a second microfluidic channel to guide a second liquid toward the fluid-interface region; and
        (iii) a capillary barrier to position a meniscus of the first liquid at the fluid-interface region using capillary force;
    (b) a first open reservoir connected to the first microfluidic channel;
    (c) a second open reservoir connected to the first open reservoir via the second microfluidic channel; and
    (d) a third open reservoir connected to the first microfluidic channel; wherein the third open reservoir is present within a fluidic path, wherein the fluidic path interconnects the first open reservoir and the fluid-interface region.

2. The apparatus of claim 1, further comprising an escape path fluidically coupled to the fluid-interface region.

3. The apparatus of claim 1, wherein the second open reservoir is connected to the first open reservoir via both the first microfluidic channel and the second microfluidic channel.

4. The apparatus of claim 1, wherein the first open reservoir comprises a leading electrolyte buffer.

5. The apparatus of claim 1, wherein the second open reservoir comprises a trailing electrolyte buffer.

6. The apparatus of claim 1, wherein the third open reservoir comprises an extraction buffer.

7. The apparatus of claim 1, wherein the first open reservoir comprises a leading electrolyte buffer for isotachophoresis (ITP); and the second open reservoir comprises a trailing electrolyte buffer for ITP.

8. The apparatus of claim 1, wherein the second microfluidic channel comprises a sample.

9. The apparatus of claim 8, wherein the sample comprises a nucleic acid.

10. The apparatus of claim 9, wherein the nucleic acid comprises DNA.

11. The apparatus of claim 9, wherein the nucleic acid comprises RNA.

12. The apparatus of claim 1, wherein the first microfluidic channel comprises a separation buffer for ITP.

13. The apparatus of claim 1, wherein either the first open reservoir or the second open reservoir comprises an electrode.

14. The apparatus of claim 1, wherein the first open reservoir comprises a first electrode and the second open reservoir comprises another electrode.

15. The apparatus of claim 1, wherein the first microfluidic channel comprises a leading electrolyte buffer with an edge that borders the fluid-interface region.

16. The apparatus of claim 1, wherein the second open reservoir is connected to the second microfluidic channel via a third microfluidic channel comprising trailing electrolyte buffer.

17. The apparatus of claim 1, wherein the third open reservoir is connected to the second microfluidic channel via the first microfluidic channel and wherein the first microfluidic channel comprises leading electrolyte buffer.

18. The apparatus of claim 1, further comprising a vacuum port positioned to release gas pressure from the fluid-interface region.

19. The apparatus of claim 1, wherein the capillary barrier is at least in part defined by a change in a cross-sectional area, wherein the change in the cross-sectional area is sufficient to arrest flow of the first liquid at the fluid-interface region.

20. The apparatus of claim 1, wherein the first microfluidic channel comprises leading electrolyte buffer and the first open reservoir comprises high buffering capacity leading electrolyte buffer.

21. A method comprising:
providing an apparatus including a structure with a first microfluidic channel to guide a first liquid toward a fluid-interface region, with a second microfluidic channel to guide a second liquid toward the fluid-interface region, and with a capillary barrier to position a meniscus of the first liquid at the fluid-interface region using capillary force;
providing a first open reservoir connected to the first microfluidic channel, a second open reservoir connected to the first open reservoir via the second microfluidic channel, and a third open reservoir connected to the first microfluidic channel; wherein the third open reservoir is present within a fluidic path, and the fluidic path interconnects the first open reservoir and the fluid-interface region; and
causing the first liquid to flow in the first microfluidic channel until the capillary barrier arrests flow of the first liquid in the first microfluidic channel.

22. The method of claim 21, further comprising causing the second liquid to flow in the second microfluidic channel until the capillary barrier arrests flow of the second liquid in the second microfluidic channel.

23. The method of claim 22, further comprising releasing gas pressure via a gas-outflow port, while flow of the first liquid is arrested.

24. The method of claim 21, wherein the first liquid is a leading electrolyte buffer.

25. The method of claim 21, wherein the second microfluidic channel comprises a sample.

26. The method of claim 21, further comprising causing the first liquid and the second liquid to contact in the fluid-interface region with the capillary barrier holding the first liquid at the fluid-interface region.

27. The method of claim 21, wherein the apparatus further comprises a third microfluidic channel comprising trailing electrolyte (TE) buffer.

28. The method of claim 21, wherein the second open reservoir comprises a trailing electrolyte buffer.

29. A method comprising:
(a) providing the apparatus of claim 1, wherein:
the first open reservoir comprises a leading electrolyte buffer; and
the first microfluidic channel comprises a leading electrolyte buffer; and
(b) introducing a sample comprising nucleic acids into the second microfluidic channel such that the sample is situated between the trailing electrolyte buffer and the leading electrolyte buffer.

30. The method of claim 29, wherein the method comprises moving the nucleic acids from the second microfluidic channel through the first microfluidic channel by applying an electrical current between the first and second open reservoirs.

31. The method of claim 29, further comprising extracting nucleic acids from the third open reservoir.

32. An apparatus, comprising:
(a) a structure comprising:
(i) a first microfluidic channel to guide a first liquid toward a fluid-interface region;
(ii) a second microfluidic channel to guide a second liquid toward the fluid-interface region; and
(iii) a capillary barrier to position a meniscus of the first liquid at the fluid-interface region using capillary force;
(b) a first open reservoir connected to the first microfluidic channel, wherein the first open reservoir or the first microfluidic channel comprises leading electrolyte buffer;
(c) a second open reservoir connected to the first open reservoir via the second microfluidic channel; and
(d) a third open reservoir connected to the first microfluidic channel; wherein the third open reservoir is present within a fluidic path, wherein the fluidic path interconnects the first open reservoir and the fluid-interface region.

33. A method comprising:
providing the apparatus of claim 32, and
introducing the second liquid into the second microfluidic channel, wherein the second liquid comprises a sample comprising nucleic acids.

* * * * *